US011471483B2

(12) United States Patent
Thomsen et al.

(10) Patent No.: US 11,471,483 B2
(45) Date of Patent: *Oct. 18, 2022

(54) IRON CARBOHYDRATE COMPLEX FOR TREATMENT OF RESTLESS LEG SYNDROME (RLS)

(71) Applicant: PHARMACOSMOS HOLDING A/S, Holbaek (DK)

(72) Inventors: Lars Lykke Thomsen, Holte (DK); Tobias S. Christensen, Copenhagen (DK); Hans Andreasen, Holbaek (DK)

(73) Assignee: PHARMACOSMOS HOLDING A/S, Holbaek (DK)

( * ) Notice: Subject to any disclaimer, the term of this patent is extended or adjusted under 35 U.S.C. 154(b) by 42 days.

This patent is subject to a terminal disclaimer.

(21) Appl. No.: 17/182,366

(22) Filed: Feb. 23, 2021

(65) Prior Publication Data
US 2021/0275580 A1 Sep. 9, 2021

Related U.S. Application Data

(62) Division of application No. 15/554,762, filed as application No. PCT/EP2016/055758 on Mar. 17, 2016, now Pat. No. 11,040,064.

(30) Foreign Application Priority Data

Mar. 19, 2015 (EP) ..................................... 15159781

(51) Int. Cl.
A61K 33/26 (2006.01)
A61K 47/61 (2017.01)

(52) U.S. Cl.
CPC .............. *A61K 33/26* (2013.01); *A61K 47/61* (2017.08)

(58) Field of Classification Search
None
See application file for complete search history.

(56) References Cited

U.S. PATENT DOCUMENTS

2004/0180849 A1 9/2004 Helenek et al.
2014/0099381 A1 4/2014 Helenek et al.

OTHER PUBLICATIONS

Garcia-Malo et al., "Quantitative transcranial sonography of the substantia nigra as a predictor of therapeutic response to intravenous iron therapy in restless legs syndrome." Sleep Med. Feb. 2020;66:123-129.
International Search Report dated May 19, 2016 issued in corresponding International Application No. PCT/EP2016/055758.
Allen, R.P. et al. "MRI measurement of brain iron in patients with restless legs syndrome." Neurology 56 (2001): 263-265.
Allen, Richard P. et al. "Clinical efficacy and safety of IV ferric carboxymaltose (FCM) treatment of RLS: A multi-centred, placebo-controlled preliminary clinical trial." Sleep Medicine 12 (2011): 906-913.
Allen, Richard P. and Christopher J. Earley. "Restless Legs Syndrome: A Review of Clinical and Pathophysiologic Features." Journal of Clinical Neurophysiology 18.2 (2001): 128-147.
Astrakas, L.G. et al. "T2 relaxometry and fMRI of the brain in late-onset restless legs syndrome." Neurology 71 (2008): 911-916.
Bianco, Laura E. et al. "Iron deficiency alters dopamine uptake and response to L-DOPA injection in Sprague-Dawley rats." Journal of Neurochemistry 106 (2008): 205-215.
Connor, J.R. et al. "Neuropathological examination suggests impaired brain iron acquisition in restless legs syndrome." Neurology 61 (2003): 304-309.
Connor, James R. et al. "Altered dopaminergic profile in the putamen and substantia nigra in restless leg syndrome." Brain 132 (2009): 2403-2412.
Earley, C.J. et al. "Abnormalities in CSF concentrations of ferritin and transferrin in restless legs syndrome." Neurology 54 (2000): 1698-1700.
Earley, Christopher J. et al. "The treatment of restless legs syndrome with intravenous iron dextran." Sleep Medicine 5 (2004): 231-235.
Earley, Christopher J. et al. "Repeated IV doses of iron provides effective supplemental treatment of restless legs syndrome." Sleep Medicine 6 (2005): 301-305.
Earley, Christopher J. et al. "MRI-determined regional brain iron concentrations in early- and late-onset restless legs syndrome." Sleep Medicine 7 (2006): 458-461.
Earley, Christopher J. et al. "A randomized, double-blind, placebo-controlled trial of intravenous iron sucrose in restless legs syndrome." Sleep Medicine (2008): 1-6.
Grote, Ludger, et al. "A Randomized, Double-Blind, Placebo Controlled, Multi-Center Study of Intravenous Iron Sucrose and Placebo in the Treatment of Restless Legs Syndrome." Movement Disorders 24.10 (2009) : 1445-1452.
Haba-Rubio, J. et al. "Restless legs syndrome and low brain iron levels in patients with haemochromatosis." Journal of Neurology, Neurosurgery, and Psychiatry 76 (2005): 1009-1010.
Lee, B.Y. et al. "In vivo Measurement of Iron Deficiency in Restless Legs Syndrome (RLS) with Voxel-Based R2 Relaxometry." Proceedings of the International Society for Magnetic Resonance in Medicine 15 (2007): 2170.
Macdougall, Iain C. and Peter Geisser. "Use of Intravenous Iron Supplementation in Chronic Kidney Disease." Iranian Journal of Kidney Diseases 7.1 (2013): 9-22.
Nordfjeld, Kim et al. "Pharmacokinetics of iron isomaltoside 1000 in patients with inflammatory bowel disease." Drug Design, Development and Therapy 6 (2012): 43-51.

(Continued)

Primary Examiner — Layla D Berry
(74) Attorney, Agent, or Firm — Robin L. Teskin; Baker, Donelson, Bearman, Caldwell & Berkowitz PC

(57) ABSTRACT

The present invention relates to pharmaceutical composition comprising an iron carbohydrate complex for use in a method for treatment or prevention of Restless Leg Syndrome (RLS) of a human patient, wherein the human patient prior to treatment has a magnetic resonance phase imaging of 0.02 radians above the average value of a control group in the substantia nigra, thalamus, putamen, or pallidum. The invention provides a higher probability for a RLS patient being treated to experience a relief in symptoms.

20 Claims, No Drawings

(56) References Cited

OTHER PUBLICATIONS

O'Keeffe, S.T. et al. "Iron Status and Restless Legs Syndrome in the Elderly." *Age and Aging* 23 (1994): 200-203.

Ondo, William G. "Intravenous iron dextran for sever refractory restless legs syndrome." *Sleep Medicine* 11 (2010): 494-496.

Pedroso, Josë Luis et al. "Severity of restless legs syndrome is inversely correlated with echogenicity of the substantia nigra in different neurodegenerative movement disorders. A preliminary observation." *Journal of the Neurological Sciences* 319 (2012): 59-62

Piniero, Domingo J. et al. "The Intracellular Location of Iron Regulatory Proteins is Altered as a Function of Iron Status in Cell Cultures and Rat Brain." *Journal of Nutrition* 131 (2001): 2831-2836.

Rizzo, Giovanni et al. "Low Brain Iron Content in Idiopathic Restless Legs Syndrome Patients Detected by Phase Imaging." *Movement Disorders* 00.00 (2013): 1-5.

Sampaio, Ana Flávia S. et al. "Iron toxicity mediated by oxidative stress enhances tissue damage in an animal model of diabetes." *Biometals* 27 (2014): 349-361.

Sloand, James A. et al. "A Double-Blind, Placebo-Controlled Trial of Intravenous Iron Dextran Therapy in Patients With ESRD and Restless Legs Syndrome." *American Journal of Kidney Diseases* 43.4 (2004): 663-670.

Snyder, Amanda M. et al. "Mitochondrial Ferritin in the Substantia Nigra in Restless Legs Syndrome." *Journal Journal of Neuropathology and Experimental Neurology* 68.11 (2009): 1193-1199.

Sun, Erica R. et al. "Iron and the Restless Legs Syndrome." *Sleep* 21.4 (1998): 381-387.

Trenkwalder, Clauder et al. "Treatment of Restless Legs Syndrome: An Evidence-Based Review and Implications for Clinical Practice." *Movement Disorders* 23.16 (2008): 2267-2302.

Unger, E.L. et al. "Effects of IV Iron Isomaltoside-1000 Treatment on Regional Brain Iron Status in an Iron-Deficient Animal." *Neuroscience* 246 (2013): 179-185.

IRON CARBOHYDRATE COMPLEX FOR TREATMENT OF RESTLESS LEG SYNDROME (RLS)

CROSS-REFERENCE TO RELATED APPLICATIONS

This application is a divisional of U.S. application Ser. No. 15/554,762, filed Aug. 31, 2017, which is a U.S. Nat'l Phase application of Int'l Appl. No. PCT/EP2016/055758, filed Mar. 17, 2016, which claims priority to European Patent Application No. EP 15159781.2, filed Mar. 19, 2015, each of which is hereby incorporated by reference herein in its entirety.

FIELD OF THE INVENTION

The present invention relates to a pharmaceutical composition comprising an iron carbohydrate complex for use in a method for treatment or prevention of Restless Leg Syndrome (RLS) of a human patient.

BACKGROUND

Restless Legs Syndrome (RLS) is a frequently occurring neurological disease, which has significant influence on the sleep quality and quality of life for the patients. RLS is classified as a neurological disease and is also known as Ekbom's syndrome.

RLS occurs in an idiopathic form with an unknown etiology (also referred to as primary RLS) and in a less frequent secondary form, related to pregnancy, anemia, kidney diseases, etc. Primary RLS is a cronical condition characterized by a painful sensation in the limbs and an irresistible urge to move the limbs to alleviate the motoric symptoms. The pain is sensed most often in the legs and less frequently in the arms. The painful sensation and the unpleasant urge to move the extremities often forces the patients to wandering about restlessly.

About 80% of the RLS patients sense nocturnal motoric phenomenon's involving periodic limb movements of sleep (PLMS). The movements may affect one or both legs and may wake the patient during the night. In moderate to severe incidents these movements often spoil the sleep. As a result, the patients feel tired during the day time and less able to perform mentally.

RLS is diagnosed based on the presence of 4 clinical criteria: (1) an irresistible urge to move the limbs often accompanied by unpleasant painful sensations in the limbs, (2) The symptoms are often sensed during rest or inactivity, such as in sitting or lying position, (3) the urge to movement and the unpleasant sensation are often alleviated when the patient walks around, and (4) the symptoms are worse at night and/or during the night time compared to the day time or the symptoms occurs only in the evening or night. The diagnosis is supported by the occurrence of RLS in a close relative, by a positive response to a dopaminergic medication, and by the presence of periodic legs movement (PLM).

The severeness of RLS is evaluated according to the International Restless Legs Scale (IRLS) based on the responses to 10 questions. The scoring results in a diagnose of mild, moderate, severe, or very severe RLS.

Lack of iron and reduced dopamine synthesis in the brain are important factors in RLS. Thus, a frequently used treatment of RLS involves dopaminergic products. The side effects are significant, however. Therefore, the focus of supplying iron to the brain has received increased attention.

RLS patients have 65% less cerebral spinal fluid (CFS) ferritin (an important iron storage protein) and three-fold more CSF transferrin (iron transport protein in blood and body fluids), despite normal serum levels of ferritin and transferrin in both RLS and controls (Earley C J, Connor J R, Beard J L, Malecki E A, Epstein D K, Allen R P (2000): Abnormalities in CSF concentrations of ferritin and transferrin in restless legs syndrome. Neurology 54: 1698-700). Iron concentrations vary throughout the brain and it has been shown that RLS patients have less iron in the substantia nigra and in the putamen parts of the brain, both sites of dopamine synthesis (Allen R P, Earley C J. (2001) Restless legs syndrome: a review of clinical and pathophysiologic features. J Clin Neurophysiol 18: 128-147). In general, decreased ferritin levels are indicative of RLS severity (O'Keeffe S T, Gavin K, Lavan J N. (1994) Iron status and restless legs syndrome in the elderly. Age Ageing 23: 200-203, and Sun E R, Chen C A, Ho G, Earley C J, Allen R P. (1998) Iron and the restless legs syndrome. Sleep 21: 371-377). These observations indicate that the ability of the brain to transport or store iron is abnormal in idiopathic RLS.

A pathological study showed that RLS patients' substantia nigra had higher mitochondrial ferritin levels and less cytosolic H-ferritin. (Snyder A M, Wang X, Patton S M, et al. Mitochondrial ferritin in the substantia nigra in restless legs syndrome. J Neuropathol Exp Neurol. 2009; 68:1193-1199). Reduced brain iron in RLS patients is also suggested by data from magnetic resonance (MR) studies exploiting the effect of iron on T2, T2*, and T2'.

The iron deficiency in the brain has been detected by neuropathological data, showing alterations of iron regulatory proteins in neuromelanin cells from brains of RLS patients (Connor J R, Boyer P J, Menzies S L, et al. Neuropathological examination suggests impaired brain iron acquisition in restless legs syndrome. Neurology. 2003; 61:304-309).

Intravenous administration of iron circumvents the problems and ineffectiveness of orally-administered iron for RLS patients. In fact, intravenous administration of iron dextran solutions, such as INFeD® (Watson Pharma, Inc.; Corona, Calif. (having an average apparent molecular weight of 165,000 g/mol), and Dexferrum® (American Regent Inc., Shirley, N.Y.) treats RLS in some instances. However, the number of successful treatments are low (Earley C J, et al: Repeated IV doses of iron provides effective supplemental treatment of restless leg syndrome, Sleep Medicine 6 (2005) 301-305). Only 50% of the RLS patients demonstrated improvement in the RLS symptoms after a single 1000 mg infusion of iron dextran.

The recent developments in phase-imaging techniques has been used to generate high contrast to cerebral iron content in patients with idiopathic RLS (Giovanni Rizzo, M D et al, Low Brain Iron Content in Idiopathic Restless Legs Syndrome Patients Detected by Phase Imaging, Movement Disorders, 2013 November; 28(13):1886-90). RLS patients were studied using gradient-echo imaging. Phase analysis was performed on localized brain regions of interest selected on phase maps, sensitive to paramagnetic tissue. Significantly higher phase values were present in the RLS patients compared with healthy controls at the level of the substantia nigra, thalamus, putamen, and pallidum, indicating reduced iron content in several regions of the brain of the patients. The results support the hypothesis of reduced brain iron content in RLS patients.

US 2004/0180849 discloses a method of treating RLS by administering to a subject an iron complex having an iron release greater than the dextran solutions, such as iron sucrose (Venofer®). The pharmacokinetic half life of iron sucrose is 5 to 6 hours, whereas iron dextran solutions like INFeD®, Dexferrum®, Cosmofer® and Imferon® has a pharmacokinetic half life of 25 to 40 hours. The high release rate, however, increase the risk of iron toxicity because of the iron overload. The iron toxicity may be due to the formation of reactive oxygen species (ROS) in body cells, such as neutrophils (Sampaio A F et al, Biometals, 2014 April; 27(2):349-61).

In addition, treatment med with iron sucrose has proved ineffective (Earley C J, et al, A randomized, double-blind, placebo-controlled trial of intravenous iron sucrose in restless legs syndrome, Sleep Medicine 2009 February; 10(2): 206-11). In the study RLS patients were administered 1000 mg iron sucrose intravenously. At 2-weeks post-treatment, iron treatment resulted in a small but significant increase in CSF ferritin and a decrease in RLS severity (GRS) but did not change PLMS or MRI iron index. There was no single case of clear treatment benefit in any of the patients.

Another iron carbohydrate, viz. Ferinject® with a relatively fast release of iron was tested in Allen R P et al, Sleep Med. 2011 October; 12(9):906-13 (Allen 2011) in the treatment of RLS patients. The pharmacokinetic half life of Ferinject® is 7.4 hours (Macdougall I A, Geisser P, Use of intravenous iron supplementation in chronic kidney disease, Iranian Journal of Kidney disease, Vol. 7, No. 1, January 2013). The background of the experiment was the inefficacy of the frequently prescribed IV iron sucrose formulation, which often failed to show lasting efficacy. In a 28 day trial 46 RLS patients were treated. 24 patients received 500 mg ferric carboxymaltose in two doses 5 days apart and 22 received a matching placebo. At day 28, those on placebo were given a single 1000 mg IV ferric carboxymaltose and those not responding to initial treatment were given a third dose of 500 mg ferric carboxymaltose. Patients were followed up for 24 weeks or until needing added RLS treatment. Of the 24 with initial iron treatment 45% responded and 29% remitted (IRLS≤10) at day 28, and 25% continued free of other RLS medications at 24 weeks after treatment. The single 1000 mg dose on day 28 produced the same degree of treatment response as the divided dose, but the added 500 mg dose for those not responding to the initial treatment showed little benefit.

A similar low success rate was obtained for infusion of iron dextran (Earley C J, Heckler D, Allen R P, The treatment of restless legs syndrome with intravenous iron dextran, Sleep Medicine 5 (2004) 231-235). In the study, 10 RLS patients were treated with intravenous iron therapy. Some of the patients experienced improvement in the RLS symptom severity, but the treatment failed to produce any response in 3 subjects who was fully treated. Analysis of the magnetic resonance imaging (MRI) showed a marginally nonsignificant increase in the substantia nigra of 0.90 l/s (P=0.059).

Based on studies on mice, it has theoretical been suggested to administrate iron isomaltoside-1000 intravenously to patients with conditions with problematic iron deficiency, e.g. RLS (Unger E L, Earley C J, Thomsen L L, Jones B C, and Allen R P, Effects of IV iron isomaltose-1000 treatment on regional brain iron status in the iron-deficient animal., Neuroscience 246 (2013) 179-185). After the injection, the NTB iron was rapidly increased in the ventral midbrain and then decreased over 12 hours to the levels observed for vehicle.

Iron isomaltoside-1000 (Monofer®) has a pharmacokinetic half life of 23.2 hours (Nordfjeld K, Andreasen H, Thomsen L L, Pharmacokinetics of Iron isomaltoside-1000 in patients with inflammatory bowel disease, *Drug Des Devel Ther.* 2012; 6:43-51).

In the prior art an effective treatment is not available for the treatment or prevention of RLS. Depending on the studio the success rate is in the range of 50-70%, which is considered too low. The present invention aims at providing a use of an iron carbohydrate complex for parenteral administering, in which the percentage of successful treatments of RLS is increased, i.e. the relative number of responding RLS patients being treated is increased.

SUMMARY OF THE INVENTION

The present invention relates to pharmaceutical composition comprising an iron carbohydrate complex for use in a method for treatment or prevention of Restless Leg Syndrome (RLS) of a human patient, wherein the human patient prior to treatment has a magnetic resonance phase imaging of 0.02 radians above the average value of a control group in the substantia nigra, thalamus, putamen, or pallidum.

To increase the chance of a successful treatment, the present inventors have found the criteria of selecting RLS patients having an unusual high magnetic resonance in one or more of four specific areas in the brain to be an effective indicator for whether an RLS patient will have a higher possibility of experiencing relief of the RLS symptoms.

In a preferred aspect of the present invention the pharmacokinetic half life ($t_{1/2}$) of the iron carbohydrate complex is 10 hours or more. This second criteria relates to the selection of the iron carbohydrate complex that will provide the desired effect. Surprisingly, a combination of these two criteria leads to improved effectiveness in the treatment of RLS patients.

According to the first criteria, human patients with relatively low iron content in the brain areas substantia nigra, thalamus, putamen, or pallidum showed an improved response when treated with an iron carbohydrate complex. The selection of RLS patients with MRI phase values of 0.02 radians above the normal level prior to treatment with the iron carbohydrate complex result in more RLS patients feeling relived of their RLS symptoms.

As a second criteria, the present inventors have found that it is important with a relatively long pharmacokinetic half life of the iron carbohydrate complex. Without being bound by theory, it is presently believed that iron or the iron carbohydrate complex is mainly entering the brain at certain time slots during a day, i.e. the brain exerts a circadian variation in the absorption of iron or the iron carbohydrate complex. Iron carbohydrate complexes with higher pharmacokinetic half life will remain for longer time in blood or plasma and thus present iron to the brain for a longer time period.

The total dose of the iron carbohydrate complex may vary in dependency of e.g. the body weight or the age of the patient. Generally, total dose of elemental iron from the iron carbohydrate complex administered to the RLS patient is 300 mg elemental iron or more. To ensure a sufficiently treatment of the patient for a long lasting effect it is generally recommended that the total dose of elemental iron from the iron carbohydrate complex administered to the RLS patient is 400 mg elemental iron or more, such as 500 mg, 600 mg, 700 mg, 800 mg, 900 mg or more. The dose of elemental iron should not exceed 3000 mg to avoid iron overload.

An aspect of the present invention is the pharmacokinetic half life of the iron carbohydrate complex. To offer the brain a sufficient amount of iron during 24 hours, it is advantageous that the pharmacokinetic half life of the iron carbohydrate complex is 10 hours or more. Suitably, the pharmacokinetic half life of the iron carbohydrate complex is 12 hours or more, such as 14 hours, 16 hours, 18 hours, 20 hours, 22 hours or more. However, the pharmacokinetic half life of the iron carbohydrate complex should not be too high, such as above 40 hours, to ensure availability of iron. In certain embodiments of the inventions the pharmacokinetic half life may be lower, such as 9 hours, 8 hours, 7 hours, 6 hours, 5 hours, or more. If a low pharmacokinetic half life is chosen, it may be beneficial to deliver a dosage 2 or more times during a day. Each dosage administration should be distanced at least 4 hours from the previous administration.

The iron carbohydrate complex may be considered a vehicle for transportation of iron to the brain. Usually, the iron carbohydrate complex is selected from the group comprising iron carboxymaltose, iron polyglucose sorbitol carboxymethyl ether complex, iron dextran, iron hydrogenated dextran, iron gluco-oligosaccharides, iron reduced gluco-oligosaccharides, iron oxidated gluco-oligosaccharides, iron carboxyalkylated reduced oligo- and poly saccharides, iron dextrin, iron hydrogenated dextrin, iron polymaltose, iron hydrogenated polymaltose, iron polyisomaltose, iron hydrogenated polyisomaltose, iron oxidised dextrin, iron oxidised dextran, or mixtures thereof. In a preferred aspect of the invention the iron carbohydrate complex is iron hydrogenated dextran, iron hydrogenated polyisomaltose, iron oxidised dextrin, or iron oxidised dextran.

The iron carbohydrate complex may originate from various sources and be processed in accordance with a multitude of methods. Some dextran types are suspected of being immunogenic and to be the reason for anaphylactic shock. It is believed that the reason for the immunogenic tendency observed for some types of dextrans is due to the presence of branches of glucose units linked to the backbone through α-1,3 glycosidic linkages. Thus, in an embodiment of the present invention the iron carbohydrate complex is iron hydrogenated dextran having a carbohydrate component comprising a backbone of glucose units linked by α-1,6 glycosidic linkages and optionally branches of glucose units linked to the backbone through α-1,3 glycosidic linkages, wherein the proportion of α-1,3 glycosidic linkages to α-1,6 glycosidic linkages is less than 2:100, such as less than 1:100. The low amount of branches of glucose units linked to the backbone through α-1,3 glycosidic linkages may have less tendency to provoke an immunological response to the treatment. In a preferred aspect of the invention the carbohydrate component does not comprise detectable branches of glucose units linked by α-1,3 glycosidic linkages to the backbone. According to the theory, the absence of detectable α-1,3 glycosidic linkages should avoid any immunological reaction due to antibodies raised in the body towards dextran or dextran-like molecules.

In a preferred embodiment of the invention, the iron carbohydrate complex is (1→6)-α-D-glucopyranan-(1→6)-D-glucitol iron(III) complex.

The iron carbohydrate complex may be produced with various lengths of the carbohydrate component. In a certain aspect the weight average molecular weight (MW) of the carbohydrate component of the iron carbohydrate complex is 800 to 40,000 Dalton, such as 800 to 10,000, and preferably 800 to 2,000 Dalton. In a preferred aspect of the invention, the weight average molecular weight of the carbohydrate component is around 1,000 MW. An iron carbohydrate complex prepared from this particular carbohydrate component has high storage stability as well as a suitable pharmacokinetical half life. Generally, the apparent molecular weight of the iron carbohydrate complex measured relative to dextran standards, is 400,000 Dalton or less, such as 300,000 Dalton or less, and preferably 200,000 Dalton or less. The method of determining the apparent molecular weight using dextran standards is disclosed in Jahn M R, et al, European Journal of Pharmaceutics and Biopharmaceutics 78 (2011) 480-491.

According to an embodiment of the present invention, pharmaceutical composition is a liquid formulation suitable for parenteral injection or infusion, optionally after appropriately being diluted. In another aspect of the invention the pharmaceutical composition is a powder capable of being dissolved in a suitable liquid for the preparation of a medicament to be delivered parenterally to a human patient.

The total dosage used in the present invention may be administered as a single dosage or in multiple dosages. To increase the patient compliance and the general desire of effective treatment, it is generally desirable to deliver the iron carbohydrate complex in a single dosage.

The pharmaceutical composition of the present invention may be administered to the RLS patient parenterally, e.g. by intravenous injection or infusion. In a certain aspect, the pharmaceutical composition is infused into a patient during 3-30 min, such as 5 to 25 min, and preferable 10-20 min.

To elect the RLS patients suitable for the treatment with the iron carbohydrate complex, the RLS patient is subjected to magnetic resonance (MR) phase imaging to evaluate brain iron content in specific areas of the brain: substantia nigra, thalamus, putamen, and/or pallidum. The technique uses tissue magnetic susceptibility differences to generate a contrast different from that of the spin density, $T_1$, $T_2$, and $T_2^*$. T1 denotes the spin-lattice and T2 the spin-spin relaxation. The method is a sensitive tool to quantify cerebral iron content. It measures phase shift in the gradient-echo images, which, measured in radians, are inversely correlated with iron content. Tissue-containing paramagnetic iron exhibits a negative phase in complex images compared with immediate adjacent tissue, which will have an increased phase. A suitable apparatus is a 1.5 Tesla GE.

According to the invention the RLS patient is suitable for treatment with the iron carbohydrate complex if the magnetic resonance phase imaging is 0.02 radians above the average value of a control group in the substantia nigra, thalamus, putamen, or pallidum. If a control group is not available the following guiding phase values for normal persons may be used:

Substantia nigra: −0.103
Thalamus: −0.069
Putamen: −0.146
Pallidum: −0.182

Suitably, the human patient prior to treatment has a magnetic resonance phase imaging of 0.03 radians above the average value of a control group in the substantia nigra, thalamus, putamen, or pallidum. Preferably, human patient prior to treatment has a magnetic resonance phase imaging of 0.04 radians above the average value of a control group in the substantia nigra, thalamus, putamen, or pallidum.

While the phase value may be measured in any of the four areas of the brain the best result is generally obtained when the magnetic resonance phase imaging value is measured in the substantia nigra.

For some patents patients the symptoms of RLS may recur after an initial treatment. For patients responding to the treatment, the effect last on average at least 3 months, such as at least 4 months and preferably at least 5 months. If the symptoms of RLS recur, the patient may be subjected to a further administration of the iron carbohydrate complex if one or more of the symptoms of RLS recurs. To prevent recurring of the RLS symptoms a patient which have received a previous treatment may be subjected to a prophylactic treatment. Suitably, the further administration is performed 1 month to 12 months after the previous administration. Thus, the further treatment may occur every $3^{rd}$ months, $4^{th}$ months, $5^{th}$ months, 6 months, or later.

EXAMPLE 1

Female mice from Strain 40 of the BXD/Ty RI recombinant inbred strain panel were used in this study. All mice were bred at the Pennsylvania State University. Female strain 40 mice were fed a pelleted, iron-deficient diet (5 mcg/g iron; Teklad TD 8096) beginning on postnatal day (P) 21 (weaning) until they were euthanized. Mice were housed in an isolated environment in groups of two-per cage in a temperature controlled (22° C.) and humidity-controlled (50%) room with an automatic 12/12-h light/dark cycle (light 0600-1800 h). All mice received food and deionized distilled water ad libitum. Experimental protocols followed the National Institutes of Health Animal Care Guidelines and were approved by the Pennsylvania State University Institutional Animal Care and Use Committee.

Iron isomaltoside-1000 (Pharmacosmos A/S, Holbaek Denmark) consists of iron and a carbohydrate moiety with tightly bound iron in the iron-carbohydrate formulation and was used in the present experiment. The control vehicle consisted of sterile phosphate-buffered saline (PBS).

Mice were assigned to one of two treatments, either Iron isomaltoside-1000 or vehicle that was injected into the tail vein 3 h before the end of the dark (active) period (06:00 h) at 90 days post weaning (P90). For injections, mice were warmed with a heating blanket and then mildly restrained to locate the tail vein using a red lamp. Iron isomaltoside-1000 was prepared in sterile PBS in an amount scaled to match that used in humans at a dose of 1000 mg iron per person (assumed average size person of 75 kg), which results in a total murine dose of about 0.27 mg.

Two experiments were conducted in this study: (1) Sequential evaluation of extracellular iron in the ventral midbrain (VMB) during 24 h before and 48 h after treatment using microdialysis techniques and (2) analyses of brain and peripheral iron concentrations at the times of euthanasia which were 3 h before the end of the dark period at either 3 or 10 days after iron injection. The microdialysis measures non-transferrin-bound (NTB), extracellular iron only in the VMB, while the post-euthanasia studies measure total tissue iron concentrations in multiple brain regions.

A CMA microdialysis probe with a 60-kd MW cutoff was implanted into the right VMB 4 days prior to iron injections according to previously described procedures (Bianco L E, Wiesinger J, Earley C J, Jones B C, Beard J L (2008) Iron deficiency alters dopamine uptake and response to L-DOPA injection in Sprague-Dawley rats. J Neurochem 106:205-215). All placements were verified in Cresyl Violet-stained brain tissue slices after euthanasia. Mice with probe placement outside of the substantia nigra were excluded from the study. Starting 24 h before iron or vehicle injection, dialysate was collected at a rate of 1.3 ll/min, and individual collection periods were 180 min long to allow for adequate sample volumes for iron analysis. Sampling continued for 48 h post-injection, resulting in a total of 24 samples per mouse. Dialysate was diluted 1:3 in ultrapure nitric acid and iron measured by atomic absorption spectroscopy (Perkin Elmer Analyst 600) according to established laboratory procedures (Pinero D J, Li N, Hu J, Beard J L, Connor J R (2001). The intracellular location of iron regulatory proteins is altered as a function of iron status in cell cultures and rat brain (J Nutr 131:2831-2836.). All standard curves exceeded $r^2 > 0.99$.

Regional brain and peripheral iron-related analyses were done in mice that were euthanized at 3- and 10-days post-injection. The mice that were euthanized at 3 days post-injection, were those that were used in the microdialysis experiments. The dialysis cannula had been placed in the right side of the VMB while the left side of the brain regions was used for all post-euthanasia evaluations.

At the time of euthanization, mice were weighed and blood samples were collected. Whole blood was analyzed for Hgb levels. Serum was collected to assess for serum iron, total iron binding capacity (TIBC) and percent transferrin saturation (Tsat). Liver and spleen were removed, weighed, and analyzed for iron content.

TABLE 1

Peripheral iron measures, average ± SD

| | 3 Days post injection | | | 10 Days post injection | | |
|---|---|---|---|---|---|---|
| Measure | Saline | Iron isomaltoside | t, p | Saline | Iron isomaltoside | t, p |
| Sample size | 9 | 8 | | 10*** | 11 | |
| Body weight (g) | 19.7 ± 0.7* | 17.1 ± 2.9** | Ns | 21.0 ± 1.3 | 20.8 ± 1.8 | Ns |
| Hemoglobin (g/dl) | 8.4 ± 1.0 | 10.2 ± 1.4 | t = 2.87, p = 0.006 | 9.0 ± 1.4 | 11.2 ± 1.6 | t = 3.32 |
| Serum iron (mcg/dl) | 177.6 ± 47.8* | 231.3 ± 21.4 | t = 3.1, p = 0.004 | 180.7 ± 36.7 | 265.5 ± 121.9**** | t = 1.81 |
| TIBC | 646.6 ± 82.4 | 603.3 ± 130.4 | Ns | 580.2 ± 161.5 | 498.5 ± 80.6 | Ns |
| Tsat | 27.0 ± 5.4 | 40.3 ± 10.9 | t = 2.9, p = 0.006 | 32.1 ± 7.2 | 51.5 ± 22.5**** | t = 2.45 |

Ns = p > 0.10.
Normal hemoglobin iron-sufficient diet = 10.94 ± 1.0 (SD).
Normal Tsat iron-sufficient diet = 37.0 ± 6.2 (SD).
Normal values for BxD strains from Jones et al. (2007) (23).
*n = 10 for serum iron but one measurement was lost for technical reasons for all other measures and body weight was not obtained on two mice leaving n = 8.
**n = 6, body weight was not obtained on 2 mice.
***There were 11 mice studied but for technical reasons these measurements were obtained from only 10 for hemoglobin and TIBC and from only nine for serum iron and Tsat %.
****n = 10, one measurement lost for technical reasons.

After euthanization, brains were extracted from the skull, weighed, and bisected at the midline. Left hemispheres were then dissected into six regions: VMB, NA, CP, PFC, CB and pons. All remaining brain tissue from the left hemisphere was collected in a separate tube. Brain regions were homogenized 1:10 in PBS-containing protease inhibitors (Roche). The regional brain iron homogenates were digested in concentrated nitric acid and analyzed for iron content by atomic absorption spectrometry (Perkin Elmer AAnalyst 600).

All statistical analyses were between vehicle and iron injected groups in each condition using unequal variance t-tests. One-tailed test for the expected direction of change, assuming increased iron, was used to improve sensitivity of the analyses. Analyses of microdialysis data used a sequential step-down approach starting at the first analysis after the injection and continuing until the first time point when the differences were not significant (pP0.05). This keeps type 1 error at 0.05 for the analyses. Analyses of differences between treatment groups were made for the iron content in each of six brain areas. The primary analyses were for differences in brain iron content over these six areas with the significance value set at p<0.0056 (Bonferroni correction). For exploratory analyses statistical differences are presented and significance values less than 0.10 were noted. All other analyses were considered exploratory with statistical comparisons recorded and statistical significance defined as p<0.05, noting the need to replicate any of the exploratory findings in future studies. Historic data are available for regional brain iron content for this strain of female mice that had been maintained on a regular iron-replete diet and euthanized at 3 months of age. These are provided in the figures for comparison purposes but were not used for any of the statistical analyses.

Based upon our previous work and assuming effect sizes of 1.5 SD, with alpha=0.05, two comparison groups per analysis and eight mice per group yields power >80%. Studies were conducted so that there would be data for the primary measures from at least eight mice in each group adjusting for data lost for these technically difficult measurements. The primary comparisons are between the two treatment groups (iron isomaltoside and vehicle) for each analysis.

Results

At 3 and 10 days post-injection Hgb, serum iron and Tsat were significantly higher for iron than vehicle-injected mice (Table 1). Body weight and TIBC did not differ significantly between treatment groups at either time point. Spleen and liver iron contents were obtained on all but one or two mice in each condition and were significantly higher for iron than vehicle-injected mice at both 3 and 10 days post-injection (Table 2). There were no significant differences in spleen or liver weights.

TABLE 2

Liver and spleen weights and iron concentrations (average ± SD)

| | 3 days post injection | | | 10 Days post injection | | |
|---|---|---|---|---|---|---|
| Measure | Saline | Iron isomaltoside | t, p | Saline | Iron isomaltoside | t, p |
| Sample size* | 8 | 8 | | 9 | 9 | |
| Liver weight (g) | 0.44 ± 0.17 | 0.34 ± 0.16 | Ns | 0.57 ± 0.11 | 0.50 ± 0.21 | Ns |
| Liver iron (mcg/g tis) | 30.2 ± 5.2 | 57.5 ± 20.2 | t = 3.2, p = 0.003 | 23.9 ± 3.9 | 34.2 ± 4.9 | t = 4.9, p < 0.0001 |
| Spleen weight (g) | 0.082 ± 0.035 | 0.059 ± 0.04 | Ns | 0.055 ± 0.031 | 0.052 ± 0.021 | Ns |
| Spleen iron (mcg/g tissue) | 86.6 ± 67.2 | 216.8 ± 91.0 | t = 3.2, p = 0.003 | 87.1 ± 31.2 | 139.0 ± 35.9 | t = 3.13, p = 0.004 |

Ns = $p > 0.10$.
*Liver and spleen measurements were obtained from only these mice for each condition.

The mean non-transferrin bound (NTB), extracellular iron content in the VMB for every hour over 1 day before and 2 days after injection with vehicle (n=9) or iron isomaltoside (n=8) were determined. There was a notable strong circadian oscillation in VMB iron for the 24-h period before iron treatment: NTB, extracellular iron increases by about 50% during the light (inactive) cycle. The iron treatment occurred, as planned, soon after the low point of the VMB iron content and on the ascending iron curve as shown in the saline-treated mice. Within the first hours after the iron injection, the NTB extracellular iron increased with the peak values at 6 h after injection. This increase was followed by a rapid decrease to normal (vehicle) levels by 12 h after injection. The iron is significantly higher ($p<0.05$) for the iron- than vehicle-treated groups at sequentially tested, 6 and 9 but not 12 h after the injection. The nonsignificant difference at 12-h, post-injection point stopped, per design, further statistical comparisons of the data at later time points.

VMB and NA total tissue iron concentrations were significantly increased for the iron-compared to vehicle-injected mice at 3 and 10 days post-injection (Table 3).

TABLE 3

Regional brain weight (g) and iron content (mcg/g tissue) average ± SD

| | 3 Days post injection | | | 10 Days post injection | | |
|---|---|---|---|---|---|---|
| Measure | Saline | Iron isomaltoside | t, p | Saline | Iron isomaltoside | t, p |
| Sample size | 9 | 8 | | 11 | 11 | |
| Brain weight | 0.25 ± 0.03 | 0.32 ± 0.12 | Ns | 0.50 ± 0.03 | 0.48 ± 0.03 | Ns |
| Ventral midbrain iron | 12.9 ± 2.3* | 16.7 ± 2.4 | t = 3.4, p = 0.002 | 12.8 ± 2.1 | 18.2 ± 3.1 | t = 5.0 p = 0.0001 |
| Nucleus accum. iron | 10.9 ± 3.2 | 17.1 ± 7.0 | t = 2.17 p = 0.0001 | 13.4 ± 2.3 | 18.2 ± 3.0 | t = 4.2 p = 0.0002 |
| Caudate-put. iron | 15.8 ± 4.8 | 18.8 ± 7.6 | Ns | 14.8 ± 4.0*** | 17.3 ± 4.3 | t = 1.4, p = 0.096 |
| Prefrontal cortex iron | 12.9 ± 4.3 | 12.0 ± 2.4** | Ns | 17.0 ± 3.5 | 16.9 ± 5.0 | Ns |
| Pons iron | 16.9 ± 5.2 | 18.2 ± 6.1 | Ns | 18.8 ± 5.4 | 21.8 ± 5.0*** | Ns |
| Cerebellum iron | 18.8 ± 5.3 | 18.8 ± 4.3** | Ns | 18.6 ± 3.2 | 20.7 ± 6.2 | Ns |

Ns = $p > 0.10$.
*n = 10, data were available for all 10 mice for VMB, but one measurement was lost for technical reasons for all other measures 3-days post saline injection.
**n = 7, data were lost for technical reasons for one mouse.
***n = 10, data were lost for technical reasons for one mouse.

The values from prior analyses of iron-sufficient female BXD strain 40 are historic data for a general comparison in all brain regions. Tissue iron levels in CP, PFC, pons and CB did not differ significantly between iron- and vehicle-treated mice at either postinjection time (Table 3). These values were compared with the historic data from iron-sufficient same strain mice.

Comparison of brain and peripheral measures at 3 days versus 10 days post-injection showed only two significant differences. PFC iron content following iron injection was significantly greater at 10 days than at 3 days post-injection (t=2.8, $p<0.015$). Peripheral measures showed significantly less liver iron (t=2.8, $p<0.015$) at 10 days than at 3 days post-injection. These significance levels were not corrected for the six brain and nine peripheral measures examined.

DISCUSSION

This study provides the first evaluation of the effects of clinically relevant doses of IV iron on regional brain iron and demonstrates two statistically significant and potentially clinically significant findings. The first of these findings is that iron isomaltoside-1000 treatment produced the expected increase in VMB iron to approximately the levels normally observed in iron sufficient mice and did not produce an iron overload in this or other areas studied. This increase persisted for at least 7 days despite the continued application of the ID diet. Thus, this IV iron treatment provided a reasonably stable duration of effect lasting at least 10 days without iron overload in the areas studied. The differences in iron content in the NA were not expected. This area has received little attention in prior animal studies of iron deficiency and has not been evaluated in RLS patients. The NA from ID mice showed much less iron compared to iron-sufficient nimals and significantly more after IV iron compared to the vehicle treatment. This unexpected finding should be evaluated further for possible clinical significance for both RLS and iron deficiency. By day 10, none of the other brain regions with the exception of CP showed any tendency for increased iron concentration following iron treatment. The CP tissue iron concentration at post-infusion day 10 was higher in the iron-versus vehicle-treated group. Although this difference was not significant ($p<0.10$), the effect size of about 0.6 suggests that larger sample sizes of about 35 would be needed for adequate power to test these differences. The iron infusion produced CP iron levels approximating those seen for the iron sufficient mice and thus the iron change at day 10 in CP could be interpreted as "normalization" of iron concentration rather than iron-overload effect.

The second major finding comes from the microdialysis data, which demonstrates for the first time a pronounced circadian oscillation in VMB NTB extracellular iron. This shows that at least in the VMB, the homeostatic mechanisms controlling extracellular iron are more dynamic than previously believed. The microdialysis study also demonstrates that VMB NTB extracellular iron is almost immediately influenced by the increase in blood iron concentrations resulting from iron treatment and is then quickly "normalized" within 12 h levels. What is not clear is whether this normalized iron is a result of cellular uptake, changes in iron import/export at the level of the blood-brain barrier or a combination of both factors. By day 3, total tissue iron concentrations in VMB were increased, so at least cellular uptake plays some role. Equally unclear is whether the VMB iron changes would have differed if the infusion had been given at the peak rather than trough of the VMB iron cycle. This may hold clinical relevance as the time of an iron infusion may determine whether the IV iron treatment achieves its maximum benefits in restoring brain iron.

The peripheral changes in the serum iron and Hgb after iron treatment were those expected and, like the iron increases in VMB, persisted for several days. The iron isomaltoside-1000 formulation appears to provide a persisting increase in iron status. This persistence may reflect a cellular response to this particular formulation of iron that effectively provides storage for later release to meet iron needs not provided by the ID diet. This may not occur for other iron formulations. This iron isomaltoside 1000 formulation like iron dextran and ferric carboxymaltose has a much stronger iron-carbohydrate bond than does iron sucrose. The clinical studies in RLS show a limited if any response to iron sucrose (Earley C J, Horska A, Mohamed M A, Barker P B, Beard J L, Allen R P (2009) A randomized, double-blind, placebo-controlled trial of intravenous iron sucrose in restless legs syndrome. Sleep Med 10:206-211.; Grote L, Leissner L, Hedner J, Ulfberg J (2009) A randomized, double-blind, placebo controlled, multi-center study of intravenous iron sucrose and placebo in the treatment of restless legs syndrome. Mov Disord 24:1445-1452.) while having substantial better responses to the iron formulations that had the tighter iron-carbohydrate binding. The effects of these various formulations on brain iron should be explored in this animal model of RLS to determine relative efficacy and safety.

The results of this study are particularly significant for RLS treatment. RLS patients have been found in many studies to have significant reduction in markers of brain iron that are most consistent and pronounced for the substantia nigra (Allen R P, Barker P B, Wehrl F, Song H K, Earley C J (2001) MRI measurement of brain iron in patients with restless legs syndrome. Neurology 56:263-265., Haba-Rubio J, Staner L, Petiau C, Erb G, Schunck T, Macher J P (2005) Restless legs syndrome and low brain iron levels in patients with haemochromatosis. J Neurol Neurosurg Psychiatry 76:1009-1010., Earley C J, B Barker P, Horska A, Allen R P (2006) MRI-determined regional brain iron concentrations in early- and late-onset restless legs syndrome. Sleep Med 7:458-461.), a primary iron-containing area of the VMB of these mice. Reductions in iron in the VMB area are associated with dopaminergic changes in rodents that parallel those observed in RLS patients (Connor J R, Wang X, Allen R P, Beard J, Wiesinger J A, Felt B T, Earley C J (2009) Altered Dopaminergic Profile in the Putamen and Substantia Nigra in Restless Leg Syndrome. Brain 132: 2403-2412.). These data indicate that a large dose of IV iron isomaltoside 1000 may safely reduce the VMB and presumably substantia nigra iron deficiency without overloading iron in other brain areas studied. Therefore, this may provide an effective treatment for RLS by reducing one putatively significant brain abnormality in RLS.

This study has several obvious weaknesses. The study relied partly upon comparisons with historical control data as it did not have an iron-sufficient control. In this study, iron-management proteins and cellular iron distribution were not determined, which would have provided a better understanding of the effects of iron treatment on cellular iron homeostasis in regions that had a change as well as those that did not. This was a single-dose, single-time-point study planned to assess effects of the dose most commonly used and studied for IV iron treatment of RLS in humans. Future work needs to assess different doses and the effects of treating at different times of the light-dark cycle.

EXAMPLE 2

Study Title

A phase II, 6-week, randomised, comparative, double-blind study of intravenous iron isomaltoside 1000 versus placebo in subjects with restless leg syndrome with a 3 month extension Study Design The study is a randomised, comparative, double-blind study with a 3 months extension. Subjects with restless leg syndrome (RLS) will be randomised 2:1 to one of the following treatment groups:

Group A (42 subjects): 1000 mg iron isomaltoside 1000 (Pharmacosmos, Holbæk, Denmark) Group B (21 subjects): Placebo infusion Furthermore, non-responders, who continue to meet entry requirements, will receive 1000 mg iron isomaltoside 1000 at week 6.

Background

RLS is a disorder of sensation with a prevalence of around 2-5% of the population. RLS is extremely responsive to dopaminergic agents, but a second issue is that iron deficiency states may precipitate RLS in as much as 25-30% of subjects with iron deficiency. RLS appears to be related to deficits in brain iron content and metabolism. Magnetic resonance imaging (MRI) images demonstrate a decrease in substantia nigra and red nucleus iron content. The severity of this decrease in brain iron content is correlated with the severity of symptoms.

Objectives

The primary objective of the study is to establish proof-of-concept for efficacy of iron isomaltoside 1000 in subjects with RLS.

The secondary objective is to compare the effect of iron isomaltoside 1000 on RLS symptoms in subjects with RLS.

The tertiary objectives are to compare the effect of iron isomaltoside 1000 in subjects with RLS on fatigue and Quality of life (QoL).

Endpoints

The primary endpoint of the study is to measure the change in RLS symptoms from baseline to week 6 measured by the clinical global impression (CGI) score The secondary endpoints are to compare the following in the treatment arms:
  Change in RLS symptoms from baseline to week 4 and month 2 and 3 measured by the CGI score
  Change in RLS symptoms from baseline to week 4 and 6 and month 2 and 3 measured by the International Restless Legs Scale (IRLS)
  Time from baseline to start of RLS medication
  Time from baseline to start of RLS medication or non-response (CGI≥3 at week 6)

The tertiary endpoints are to compare the following in the treatment arms:
  Change in fatigue symptoms from baseline to week 6 and month 3 measured by the Fatigue Severity Scale (FSS)
  Change in QoL from baseline to week 6 and month 3 measured by the Restless Legs Syndrome Quality of Life (RLS-QoL) questionnaire
  Change in depression and anxiety symptoms from baseline to week 6 and month 3 measured by the Hospital Anxiety and Depression scale (HADS)
  Change in sleep disturbance from baseline to week 6 and month 3 measured by the Medical Outcome Study Sleep Scale (MOSSS)
  Change in concentrations of haemoglobin (Hb), s-iron, s-ferritin, total iron binding capacity (TIBC), and transferrin saturation (TfS) from baseline to week 6 and month 3
  Regional iron distribution in the brain at baseline and 6 weeks after dosing measured by MRI
  Changes and actual scores for IRLS and CGI until start of RLS medications The safety endpoint includes:
  Type and incidence of adverse drug reactions (ADRs)
  Number of adverse events (AEs) of special interest (i.e. hypersensitivity symptoms such as: urticaria, oedema, bronchospasm, hypotension, cardiorespiratory arrest, syncope, unresponsiveness, or loss of consciousness at pre-specified time points in relation to administration of study drug)
  Change in haematology parameters, s-sodium, s-potassium, s-calcium, s-phosphate, s-urea, s-creatinine, s-albumin, s-bilirubin, aspartate aminotransferase (ASAT), and alanine aminotransferase (ALAT) from baseline to week 6 and month 3
  Change in vital signs (heart rate and blood pressure) during drug administration
  Clinical significant electrocardiogram (ECG) during drug administration Diagnostic Assessments
Cambridge-Hopkins RLS questionnaire (CH-RLSq)
Hopkins telephone diagnostic inventory (HTDI)

Efficacy Assessments

The study includes the following efficacy assessments:
CGI score
IRLS
FSS
RLS-QoL
HADS
MOS-SS
Measurements of Hb, s-iron, s-ferritin, TIBC, and TfS
MRI Safety Assessments The study includes the following safety assessments:
  AEs will be collected and evaluated for relatedness, severity, seriousness, and expectedness. They will be reported to authorities and followed-up according to international and local requirements
  Number of AEs of special interest (i.e. hypersensitivity symptoms such as: urticaria, oedema, bronchospasm, hypotension, cardiorespiratory arrest, syncope, unresponsiveness, or loss of consciousness at pre-specified time points in relation to administration of study drug) will be captured
  Standard safety laboratory parameters, vital signs, and ECG Study Duration and Number of Visits For the individual subject, there will be 4 phases to the study which includes teleconferences (TCs) and 2 visits:

Initial Contact—Pre-Screening

The initial contact includes general information of the study and a review of eligibility. If the subject meets the general eligibility (age, self-report of RLS, interested in participating, willing to come off RLS medications), a consent form will be provided together with the study information.

Screening and Medication Withdrawal

When the subject has signed and returns the consent form to the research staff, the screening and medication withdrawal phase starts. The subject is given a copy of the signed consent. The screening phase including medication withdrawal involves TCs to confirm eligibility, characterize the RLS, and arrange/support discontinuing current RLS-related medications. During this phase, the subject will have all demographic, RLS diagnostic, and RLS history forms completed and have a full medical history taken. The participant will be given an appointment to come to Johns Hopkins to start the third phase of the study at 10 days or later after discontinuing all RLS medications. The screening and medication withdrawal phase will take approximately 4 weeks, but may be much longer depending on how the subject is coping in the withdrawal phase.

Treatment and Treatment Evaluation

The treatment and treatment evaluation is the main study. This phase starts with a baseline visit at Johns Hopkins where the subject will be provided a second consent form covering the rest of the study (main study and extension study). When the subject has signed this consent, the baseline status of RLS, sleep, QoL, MRI etc. will be performed. The treatment will be given and the TCs and visit for the follow-ups will be scheduled. This phase of the study will take about 6 weeks.

3-Months Extension

After the main study, the subjects may continue in an extension of up to 3 months follow-up depending on their time for enrolment in the study.

For responders, the extension study will include up to 2 TCs (2 and 3 months).

Non-responders will receive 1000 mg iron isomaltoside 1000, and they will attend up to 4 TCs (4 and 6 weeks and 2 and 3 months).

It will be up to the discretion of the Investigator to decide the duration of the extension study for the individual subject.

Subject Population

Subjects with a diagnosis of RLS and who fulfill the following eligibility criteria will be included.

Inclusion Criteria:

A subject will be eligible for inclusion in the study if he/she fulfils the following criteria:

1. Age≥18 years
2. Diagnosis of RLS based upon the CH-RLSq and HTDI
3. IRLS score≥15 at baseline evaluation when off RLS medications
4. Willingness to participate and signing the informed consent form Exclusion Criteria:

A subject will not be eligible for inclusion in this study if he/she fulfils any of the following criteria:

1. S-ferritin>300 ng/mL and/or TfS>50%
2. Iron overload or disturbances in utilisation of iron (e.g. haemochromatosis and haemosiderosis)
3. Known hypersensitivity to IV iron or any excipients in the investigational drug products
4. Pregnant or nursing women. In order to avoid pregnancy, women of childbearing potential have to use adequate contraception (e.g. intrauterine devices, hormonal contraceptives, or double barrier method) during the whole study period and 7 days after the last dosing
5. History of active asthma within the last 5 years
6. Decompensated liver cirrhosis or active hepatitis (defined as ASAT or ALAT>3 times upper limit of normal)
7. Active acute or chronic infections (assessed by clinical judgment supplied with white blood cells (WBC) and C-reactive protein (CRP))
8. Rheumatoid arthritis with symptoms or signs of active inflammation
9. Pregnant or nursing women
10. Previous IV iron treatment for RLS
11. IV iron treatment within 1 year prior to screening
12. Blood transfusion within 4 weeks prior to screening
13. Planned elective surgery during the study
14. Participation in any other interventional study where the study drug has not passed 5 half-lives prior to the screening
15. Any other medical condition that, in the opinion of the Investigator, may cause the subject to be unsuitable for the completion of the study or place the subject at potential risk from being in the study, e.g. history of multiple allergies, a malignancy, un-controlled hypertension, unstable ischaemic heart disease, or uncontrolled diabetes mellitus Study Treatment The study drugs will be dosed as follows:

Subjects in group A will be dosed with an infusion of 1000 mg iron isomaltoside 1000 at baseline. The infusion is diluted in 100 mL 0.9% sodium chloride and given over approximately 15 min (range: 12-18 min).

Subject in group B will be dosed with a single infusion of 100 mL 0.9% sodium chloride at baseline given over approximately 15 min (range: 12-18 min).

At week 6, non-responders, who continue to meet entry requirements for the study, will be given 1000 mg iron isomaltoside 1000 administered as an infusion. The infusion is diluted in 100 mL 0.9% sodium chloride and given over approximately 15 min (range: 12-18 min).

No test dose will be applied.

Blinding will be obtained by shielding the patients from seeing preparation of the study drug and by having unblinded study personnel not involved in any study assessments (efficacy or safety) responsible for preparing and administering the study drug. This unblinded member of staff will randomize the subject, prepare, and administer study drug. Further, this unblinded member of staff will be the only one doing study drug accountability. An unblinded investigator will evaluate the blood values.

During study drug administration a blinded member of staff also shielded from seeing study drug or any procedures related hereto will be present. This blinded member of staff will ob-serve the subject and monitor any adverse events during or after study drug administration.

All used material will be removed by the unblinded member of staff without revealing the infused fluid.

Study drug accountability will be monitored by unblinded personnel.

Statistical Analyses

In an earlier study in RLS patients [Allen et. al., 2011], the CGI was very much or much improved in 48.3% of patients receiving two doses of 1000 mg IV iron carboxymaltose 5-days apart versus 14.3% in patients receiving placebo, after 28 days of treatment. In this study, 1000 mg IV iron isomaltoside 1000 will be administered, and similar response rates can be assumed.

With a 2:1 randomisation, a two-sided significance level of 0.05, power of 80%, and assuming response rates of 50% and 15%, a total of 63 patients (42 and 21 in each arm) is required to show an absolute difference between the two treatment groups.

Primary Endpoint

The primary efficacy data will be summarized using number and percentage of subjects. The risk difference, with treatment as factor and baseline CGI score as covariate, between group A and B will be used to compare the proportion of subjects with CGI very much or much improved from baseline to week 6. A logistic regression analysis with the use of treatment and baseline CGI score as covariate will be performed as sensitivity analysis.

Few drop-outs are expected during the first 6 week of treatment. In the analysis of the primary endpoint, subjects who drop out of the study before week 6 will be set as non-responders.

In order to reflect a realistic approach, RLS medication will be allowed as follows: Subjects will be allowed to use RLS medication five times during week 1-4 after baseline, but none during week 5-6. In the primary analysis, for subjects not jeopardising this rule, the CGI assessment at week 6 will be used as observed. Subjects using more RLS medication will be set as non-responders.

Secondary Endpoints

The secondary efficacy data will be summarized descriptively including the sample number, mean, SD, minimum, and maximum for continuous variables and the sample number and percentage will be calculated for all categorical data.

For continuous variables, repeated measures mixed models will be used to compare the change from baseline to specified week with the use of treatment, visit, and treatment*visit interactions as factors, and baseline values as covariates. All tests will be two-tailed and significance level will be 0.05.

For time-points after week 6, only the responding subjects will be included in the comparisons between iron isomaltoside 1000 and placebo. Data for non-responding subjects will be presented descriptively. Time from baseline to start of RLS medication and time from base-line to start of RLS medication or non-response will be evaluated by a Kaplan-Meier curve. The treatment groups will be compared by a log-rank test. Non-responding subjects is an integral part of this endpoint, and hence naturally included.

Tertiary Endpoints

The tertiary endpoints will be analysed and presented similar to the secondary endpoints, except for changes and actual scores for IRLS and CGI until start of RLS medications, which will be described descriptively.

Safety Endpoints

AEs will be summary tabulated by latest version of Medical Dictionary for Regulatory Activities (MedDRA) by body system and preferred term, indicating number and percentage of subjects and number of events. Shift tables will be generated for laboratory parameters, i.e. haematology parameters, s-sodium, s-potassium, s-calcium, s-phosphate, s-urea, s-creatinine, s-albumin, s-bilirubin, ASAT, and ALAT from baseline to subsequent visits.

Change in vital signs and ECG will be tabulated using descriptive statistics. Weight, physical condition, concomitant medication, and medical history will be listed by subject.

All the statistical analyses will be described in a statistical analysis plan.

The invention claimed is:

1. A method for treatment or prevention of Restless Leg Syndrome (RLS) of a human patient, comprising:
    (a) identifying a patient having an elevated magnetic resonance phase imaging of 0.04 radians above the normal value in the substantia nigra, thalamus, putamen, or pallidum; and
    (b) administering to the patient an effective amount of a pharmaceutical composition comprising an iron carbohydrate complex;
    wherein the iron carbohydrate complex comprises an iron reduced gluco-oligosaccharide; and
    wherein the weight average molecular weight (MW) of the carbohydrate component of the iron carbohydrate complex is 800 to 2,000 Dalton.

2. The method according to claim 1, wherein the weight average molecular weight of the carbohydrate component is around 1,000 Dalton.

3. The method according to claim 1, wherein the apparent molecular weight of the iron carbohydrate complex measured relative to dextran standards is 200,000 Daltons or less.

4. The method according to claim 1, wherein the pharmacokinetic half-life ($t_{1/2}$) of the iron carbohydrate complex is 10 hours or more, 12 hours or more, 14 hours, 16 hours, 18 hours, 20 hours, 22 hours, or more.

5. The method according to claim 4, wherein the pharmacokinetic half-life ($t_{1/2}$) of the iron carbohydrate complex is 20 hours or more, or is 22 hours or more.

6. The method according to claim 1, wherein the iron carbohydrate complex comprises a carbohydrate component comprising a backbone of glucose units linked by α-1,6 glycosidic linkages and optionally branches of glucose units linked to the backbone through a-1,3 glycosidic linkages, wherein the proportion of α-1,3 glycosidic linkages to α-1,6 glycosidic linkages is less than 2:100, or is less than 1:100.

7. The method according to claim 1, wherein the carbohydrate component does not comprise detectable branches of glucose units linked by a α-1,3 glycosidic linkages to the backbone.

8. The method according to claim 1, wherein the iron carbohydrate complex comprises (1→6)-α-D-glucopyranan-(1→6)-D-glucitol iron(III) complex.

9. The method according to claim 1, wherein the pharmacokinetic half-life ($t_{1/2}$) of the iron carbohydrate complex is 20 hours or more,
    the iron carbohydrate complex comprises (1→6)-α-D-glucopyranan-(1→6)-D-glucitol iron(III) complex,
    the weight average molecular weight (MW) of the carbohydrate component of the iron carbohydrate complex is around 1,000 Dalton, and
    the apparent molecular weight of the iron carbohydrate complex measured relative to dextran standards is 200,000 Dalton or less.

10. The method according to claim 1, wherein the iron carbohydrate complex is iron isomaltoside 1000.

11. The method according to claim 1, wherein the total dose of elemental iron from the iron carbohydrate complex administered to the RLS patient is 300 mg elemental iron or more, 400 mg elemental iron or more, 500 mg elemental iron, 600 mg elemental iron, 700 mg elemental iron, 800 mg elemental iron, 900 mg elemental iron, or more.

12. The method according to claim 1, wherein the total dose of elemental iron from the iron carbohydrate complex administered to the RLS patient is 800 mg elemental iron or more, 900 mg elemental iron or more, or is 1,000 mg elemental iron.

13. The method according to claim 1, wherein the pharmaceutical composition is a liquid formulation suitable for parenteral injection or infusion, optionally after appropriately being diluted.

14. The method according to claim 1, wherein the pharmaceutical composition is infused into a patient during a 3 to 30 minute time period, or a 5 to 25 minute time period.

15. The method according to claim 1, wherein the iron carbohydrate complex is iron isomaltoside 1000, the total dose of elemental iron from the iron carbohydrate complex administered to the RLS patient is 800 mg elemental iron or more, and the pharmaceutical composition is infused into the patient during a 3 to 30 minute time period; or wherein the iron carbohydrate complex is iron isomaltoside 1000, the total dose of elemental iron from the iron carbohydrate complex administered to the RLS patient is 1,000 mg elemental iron, and the pharmaceutical composition is administered as a single dose which is infused into the patient during a 3 to 30 minute time period.

16. The method according to claim 1, wherein the patient is subjected to a further administration of the iron carbohydrate complex if one or more of the symptoms of RLS recurs.

17. The method according to claim 16, wherein the further administration is performed 1 month to 12 months after the previous administration.

18. The method according to claim 1, wherein the normal value is a magnetic resonance phase imaging value of:
   Substantia nigra: −0.103
   Thalamus: −0.069
   Putamen: −0.146
   Pallidum: −0.182.

19. A method for treatment or prevention of Restless Leg Syndrome (RLS) of a human patient, comprising:
   (a) identifying a patient having an elevated magnetic resonance phase imaging of 0.04 radians above the normal value in the substantia nigra, thalamus, putamen, or pallidum; and
   (b) administering to the patient an effective amount of a pharmaceutical composition comprising an iron carbohydrate complex;
   wherein the iron carbohydrate complex is iron isomaltoside 1000.

20. A method for treatment or prevention of Restless Leg Syndrome (RLS) of a human patient, comprising:
   (a) identifying a patient having an elevated magnetic resonance phase imaging of 0.04 radians above the normal value in the substantia nigra, thalamus, putamen, or pallidum; and
   (b) administering to the patient an effective amount of a pharmaceutical composition comprising an iron carbohydrate complex;
   wherein the iron carbohydrate complex is iron isomaltoside 1000;
   wherein the total dose of elemental iron from the iron carbohydrate complex administered to the RLS patient is 800 mg elemental iron or more, or is 1,000 mg elemental iron; and
   wherein the pharmaceutical composition is infused into the patient during a 3 to 30 minute time period.

* * * * *